United States Patent
Mansi et al.

(10) Patent No.: US 9,814,446 B2
(45) Date of Patent: Nov. 14, 2017

(54) METHOD AND SYSTEM FOR AUTOMATIC ESTIMATION OF SHEAR MODULUS AND VISCOSITY FROM SHEAR WAVE IMAGING

(71) Applicant: Siemens Medical Solutions USA, Inc., Malvern, PA (US)

(72) Inventors: Tommaso Mansi, Plainsboro, NJ (US); Saikiran Rapaka, Pennington, NJ (US); Ali Kamen, Skillman, NJ (US); Dorin Comaniciu, Princeton Junction, NJ (US); Francois Forlot, Taupont (FR); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 236 days.

(21) Appl. No.: 14/693,080

(22) Filed: Apr. 22, 2015

(65) Prior Publication Data

US 2016/0310107 A1    Oct. 27, 2016

(51) Int. Cl.
*A61B 8/00*        (2006.01)
*A61B 8/08*        (2006.01)

(52) U.S. Cl.
CPC .............. *A61B 8/485* (2013.01); *A61B 8/463* (2013.01); *A61B 8/5223* (2013.01); *A61B 8/5207* (2013.01); *A61B 8/5269* (2013.01)

(58) Field of Classification Search
CPC ....... A61B 8/463; A61B 8/485; A61B 8/5207; A61B 8/5223; A61B 8/5269
See application file for complete search history.

(56) References Cited

U.S. PATENT DOCUMENTS

| | | | |
|---|---|---|---|
| 8,187,187 B2 | 5/2012 | Fan et al. | |
| 8,197,408 B2 | 6/2012 | Fan et al. | |
| 8,801,614 B2 | 8/2014 | Hsu et al. | |
| 2009/0007674 A1 | 1/2009 | Kwon et al. | |
| 2010/0016718 A1 | 1/2010 | Fan et al. | |
| 2012/0123263 A1 | 5/2012 | Osaka et al. | |
| 2013/0066204 A1 | 3/2013 | Fan et al. | |
| 2013/0211253 A1 | 8/2013 | Hsu et al. | |
| 2013/0218011 A1 | 8/2013 | Benson et al. | |
| 2014/0276046 A1* | 9/2014 | Kim | A61B 8/485 600/438 |

* cited by examiner

*Primary Examiner* — Mark Remaly (57) ABSTRACT

A method and system for automatic non-invasive estimation of shear modulus and viscosity of biological tissue from shear-wave imaging is disclosed. Shear-wave images are acquired to evaluate the mechanical properties of an organ of a patient. Shear-wave propagation in the tissue in the shear-wave images is simulated based on shear modulus and viscosity values for the tissue using a computational model of shear-wave propagation. The simulated shear-wave propagation is compared to observed shear-wave propagation in the shear-wave images of the tissue using a cost function. Patient-specific shear modulus and viscosity values for the tissue are estimated to optimize the cost function comparing the simulated shear-wave propagation to the observed shear-wave propagation.

35 Claims, 5 Drawing Sheets

METHOD AND SYSTEM FOR AUTOMATIC ESTIMATION OF SHEAR MODULUS AND VISCOSITY FROM SHEAR WAVE IMAGING

BACKGROUND OF THE INVENTION

The present invention relates to medical image-based estimation of mechanical tissue properties and more particularly to automatic estimation of shear modulus and viscosity of tissue from shear wave imaging.

Shear-wave imaging (SWI) is an ultrasound-based imaging modality that can provide important information about tissue structure and integrity. In SWI, an ultrasound probe is used to generate and track propagating shear waves in biological tissue. Radiation force from an acoustic radiation force impulse (ARFI) generates the shear waves in the tissue. The velocity of the shear wave propagation in the tissue is measured and a time sequence of images showing the displacement of the shear wave is captured by the ultrasound probe.

Qualitative metrics have been derived for SWI, for example to highlight stiffer or softer tissues in a region of interest. Clinical applications for SWI are numerous, especially in oncology where SWI can be used to discriminate malignant from benign lesions. However, accurate quantitative estimation of tissue elasticity and viscosity from SWI remains an important challenge. While shear modulus can be directly related to the shear wave velocity in homogenous isotropic solids, that relationship does not hold in viscous media like biological tissues where the viscosity also affects the speed of the shear wave. It is therefore important to consider both properties in the estimation process in order to achieve accurate assessment of the tissue mechanics and constitution of the tissue.

BRIEF SUMMARY OF THE INVENTION

The present invention provides a method and system for estimating patient-specific values for shear modulus and viscosity of biological tissue from shear-wave imaging (SWI). Embodiments of the present invention couple a direct model of shear-wave propagation in soft media with an optimizer algorithm to automatically estimate both shear modulus and viscosity from shear-wave images. Shear-wave displacement is computed from a forward model of shear-wave propagation, given shear modulus and viscosity. A cost function, which evaluates the difference between the computer shear-wave propagation and the observed shear-wave propagation in the shear-wave images, is then minimized, for example using a gradient free optimizer, to estimate personalized values for the shear modulus and viscosity of the tissue. Embodiments of the present invention can use a hierarchical approach, which enables estimation of spatial maps of shear modulus and viscosity, which can then be displayed to an end user for diagnostic purposes. A map obtained from initial estimation of the shear modulus from the shear-wave imaging using the homogeneous tissue approximation can also be used as initialization of the proposed approach, which estimates both shear modulus and viscosity.

In one embodiment of the present invention, shear-wave propagation in tissue of a patient is simulated based on shear modulus and viscosity values for the tissue using a computational model of shear-wave propagation. The simulated shear-wave propagation is compared to observed shear-wave propagation in shear-wave images of the tissue using a cost function. Patient-specific shear modulus and viscosity values for the tissue are estimated to optimize the cost function comparing the simulated shear-wave propagation to the observed shear-wave propagation.

These and other advantages of the invention will be apparent to those of ordinary skill in the art by reference to the following detailed description and the accompanying drawings.

DETAILED DESCRIPTION

The present invention relates to automatic estimation of shear modulus and viscosity of biological tissue from shear-wave imaging (SWI). Embodiments of the present invention are described herein to give a visual understanding of the method for estimating patient-specific values for shear modulus and viscosity of a region of tissue. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Embodiments of the present invention utilize an inverse-modeling approach to estimate patient-specific shear modulus and viscosity values from shear-wave images using a forward model of shear-wave propagation. The forward model of shear-wave propagation is employed to compute, given a set of shear modulus and viscosity parameters, and an initial condition, the shear wave displacement within a multi-dimensional grid lattice (2D/3D) whose extent covers the observed domain. The computed shear-wave propagation is then compared with the observed shear-wave propagation in the shear-wave images. If the computed shear-wave propagation does not match the observed shear-wave propagation, according to a selected cost function, an optimizer process is employed to estimate the optimal shear modulus and viscosity automatically. For example, in a possible implementation, a Normalized Cross-Correlation metric can be used as a cost function to compare the computed and observed shear-wave propagation, but any similarity metric can be used. The optimization process may be performed using a gradient-free optimizer, but the present invention is not limited thereto. A hierarchical method can be used to estimate spatially varying values for the shear modulus and viscosity over a target region of tissue. A first map of shear modulus estimates can be obtained by using the shear wave velocity, which is related to the shear modulus in non-viscous media. This map can be used to initialize the estimation procedure but also to identify the regions with varying biomechanical properties.

Figure 1:
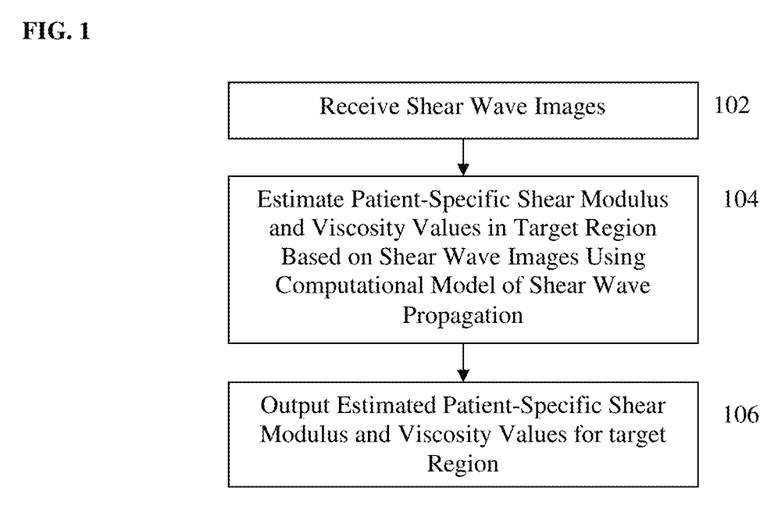
FIG. 1 illustrates a method for non-invasive estimation of shear modulus and viscosity of a target region of biological tissue according to an embodiment of the present invention.

FIG. 1 illustrates a method for non-invasive estimation of shear modulus and viscosity of a target region of biological tissue according to an embodiment of the present invention. At step 102, shear-wave images are received. Shear-wave images are acquired via shear-wave imaging (SWI), which uses an ultrasound probe to generate and track propagating shear-waves in biological tissue. Radiation force from an acoustic radiation force impulse (ARFI) generates the shear-waves in the tissue and a time-sequence of images showing the displacement of the shear-waves in the tissue over time is captured by the ultrasound probe. The shear-wave images can be a time dependent sequence of two-dimensional (2D) images or a time dependent sequence of three-dimensional (3D) images. The shear-wave images can be received directly from the ultrasound probe, or can be received by loading previously acquired shear-wave images from a memory or storage of a computer system or receiving previously acquired shear-wave images over a data network. The shear-wave images can include a target region of tissue of a patient. For example, the shear-wave images can include a region of tissue in which a tumor or lesion is present.

Figure 2:
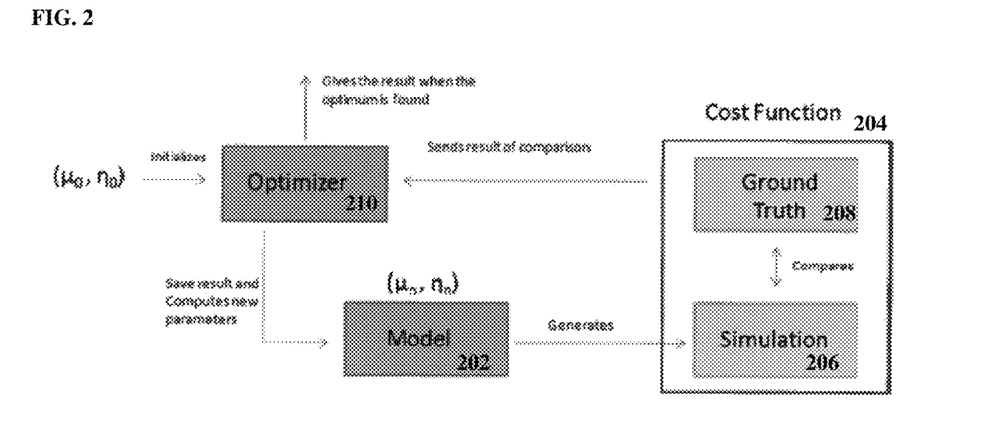
FIG. 2 illustrates a framework for estimating patient-specific shear modulus and viscosity values from shear-wave images using a computational model of shear-wave propagation according to an embodiment of the present invention.

At step 104, patient-specific shear modulus and viscosity values for tissue in a target region are estimated based on the shear-wave images using a computational model of shear wave propagation. The target region of tissue can refer to all of the tissue in the shear-wave images or can refer to a particular region of interest within the shear-wave images. FIG. 2 illustrates a framework for estimating the patient-specific shear modulus and viscosity values from the shear-wave images using a computational model of shear-wave propagation according to an embodiment of the present invention. As shown in FIG. 2, model 202 is a forward computational model of wear wave propagation. Given values for the shear modulus and viscosity ($\mu_n$, $\eta_n$) of tissue in the target region, and an initial condition, model 202 generates a simulation 206 of shear-wave propagation in the target region. The shear modulus and viscosity estimation framework is initialized with initial shear modulus and viscosity values $\mu_0$, $\eta_0$. Cost function 204 compares the simulation 206 with ground truth shear-modulus propagation 208 observed in the shear-wave images, and sends the result of the comparison to optimizer 210. Optimizer 210 computes new parameter values for the shear modulus and viscosity to minimize cost function 204 and sends the new parameter values for the shear modulus and viscosity to model 202, which generates another simulation 206 using the new parameter values. When, based on the result of the comparison calculated by cost function 204, optimizer 210 determines that the optimal values for the shear modulus and viscosity have been found that minimize cost function 204, optimizer 210 outputs the optimal values for the shear modulus and viscosity. The model 202, cost function 204, and optimizer 210 are described in greater detail in the description for the method of FIG. 3.

Figure 3:
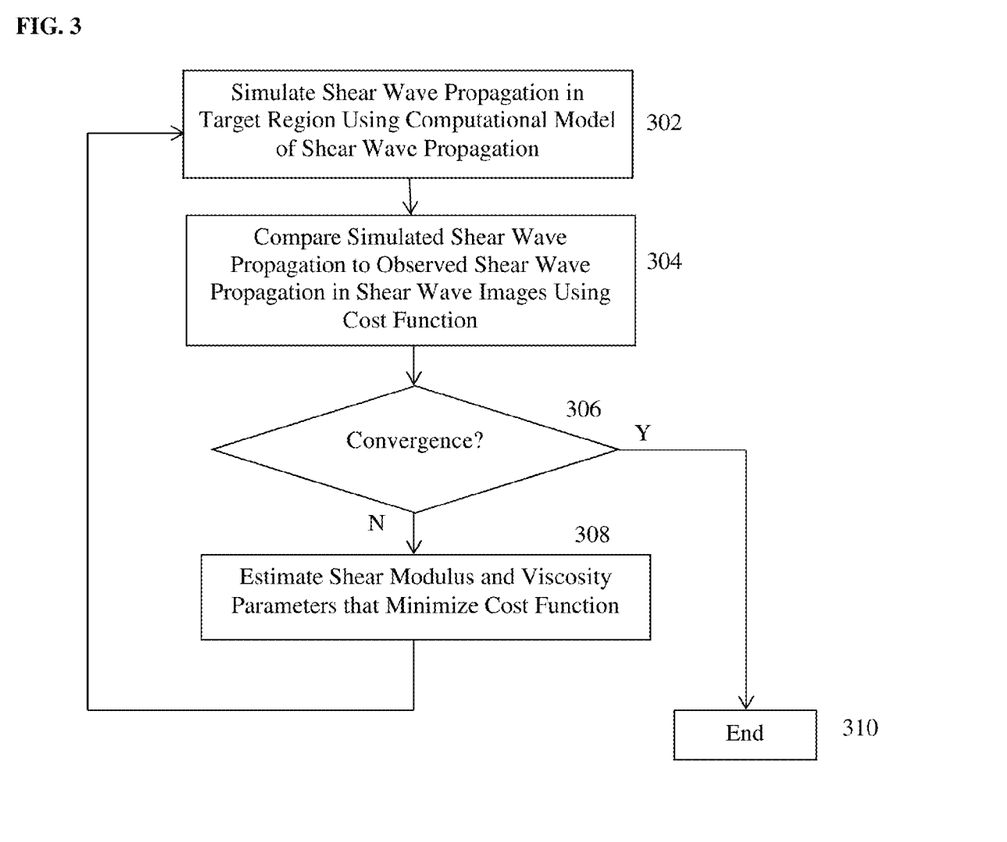
FIG. 3 illustrates a method for estimating patient-specific shear modulus and viscosity values from shear-wave images using a computational model of shear-wave propagation according to an embodiment of the present invention.

FIG. 3 illustrates a method for estimating patient-specific shear modulus and viscosity values from shear-wave images using a computational model of shear-wave propagation according to an embodiment of the present invention. The method of FIG. 3 can be used to implement step 104 of FIG. 1. At step 302, shear-wave propagation is simulated in the target region using computational model of shear-wave propagation. The computational model of shear-wave propagation computes the shear-wave displacement for given shear modulus and viscosity. To that end, the following partial differential equation for transverse waves can be used:

$$\rho \partial_t^2 u = \mu \nabla^2 u + \eta \partial_t \nabla^2 u$$

where $\mu$ is the shear modulus, $\eta$ is the viscosity, $\rho$ is the density (which can be assumed to be equal to 1070 kg/m³ in biological tissues), and u is the tissue shear displacement. The wave propagates in 1-, 2-, or 3-dimensional space according to Neumann, 0-Dirichlet, or absorbent boundary conditions defined according to the setup of the SWI acquisition. In a possible implementation, Neumann or absorbent boundary conditions can be employed by default. In another embodiment, the organ of interest is segmented from an ultrasound B-mode image. The resulting boundaries are used to set proper shear-wave boundary conditions (e.g. Neumann), while in the areas of the SWI where no boundary is visible, absorbent boundary conditions are used. The B-mode and SW images are aligned by design if the probe does not move between the two acquisitions. This could be done completely transparently to the user by the hardware. The computational model can compute the shear-wave displacement on a multi-dimensional grid lattice (2D/3D) whose extent covers the domain of the target region of tissue in the shear-wave images. As described above, the target region of tissue can be the entire shear-wave image or a region of interest defined in the shear-wave images.

In a possible implementation, generic values, such as values from literature or average values stored in database from known cases, can be used for initial values for the shear modulus and viscosity of the tissue. In another possible implementation, the shear modulus can be estimated directly from the velocity of the shear wave in the shear wave images. In this case, the viscosity can be assigned an initial value of zero or a generic value, such as a value from the literature or an average value in a database of known cases.

Initial boundary conditions are determined for the shear-wave propagation computation. In an advantageous embodiment, the first N frames of the acquired shear-wave images are used to establish initial conditions (e.g. N=2). In particular, the displacement of the observed shear wave in the first N frames of the shear-wave images provides an initial boundary condition, and then the computational model is employed to simulated propagation of the shear-wave. This ensures that the ground truth observed shear-wave in shear-wave images and the computed shear-wave start at exactly the same state, and protects against a temporal shift between the observed shear-wave and the computed shear-wave. In another possible embodiment, a direct model of the ARFI pulse is employed to determine the initial conditions of the shear-wave propagation. In this embodiment, parameters of the ultrasound probe are directly used to compute the force due to the ARFI pulse.

In an advantageous implementation, the finite element method (FEM) can be used to compute the shear-wave propagation on the 1-, 2-, or 3-dimensional space. An implicit time stepping approach can be used for increased stability. However, it is to be understood that the present invention is not limited to FEM with an implicit time steeping approach to compute the shear-wave propagation, and other methods, such as explicit FEM or finite difference methods, can be used to compute the shear-wave propagation as well. Furthermore, the present invention is not limited to using the above described differential equation for transverse wave as the shear-wave propagation model, and other shear-wave propagation models based on more complex visco-elastic material models can be used as well.

At step 304, the simulated shear-wave propagation is compared to observed shear-wave propagation in the shear-wave images using a cost function. The shear modulus and viscosity are estimated by minimizing a cost function that calculates a similarity (or difference) between the computed (simulated) shear-wave propagation and the measured (observed) shear-wave propagation in the shear-wave images. In a first embodiment, the computed shear-wave propagation is directly compared with the observed shear-wave displacement in the shear wave images. According to an advantageous implementation, normalized cross correlation (NCC) can be used as a cost function that measures a similarity between the computed and observed shear-wave propagation. However, the present invention is not limited to NCC and any other cost function, such as sum of squared distance, can be similarly employed to measure the similarity between the computed and observed shear-wave propagation. The NCC cost function can be expressed as:

$$\frac{1}{n} \sum_{x,y} \frac{(f(x,y) - \bar{f})(t(x,y) - \bar{t})}{\sigma_f \sigma_t}$$

where $\sigma_t$ is the standard deviation of the measured shear-wave propagation t(x, y), $\sigma_f$ is the standard deviation of the computed shear-wave propagation f(x, y), $\bar{t}$ is the mean of the measured data set, $\bar{f}$ is the mean of the simulation set, and n is the number of compared elements. In a possible implementation, the NCC is calculated at a user-defined (or automatically selected) time frame, over the entire domain of the target region. In this case, n refers to a number of locations (pixels/voxels), denoted as (x, y) in the above equation, at which to compare the simulated shear-wave displacement to the observed shear-wave displacement at a certain time point.

In an alternative implementation, the NCC can be calculated at a user-defined (or automatically selected) position in space over the entire temporal domain. In this case, n refers to the number of time steps at which to compare the simulated shear-wave displacement to the observed shear-wave displacement for a particular spatial location. In another possible implementation, the NCC can be calculated over the entire spatio-temporal domain.

In a second embodiment, as an alternative to the cost function directly comparing the simulated and observed shear-wave propagation, indirect estimation can be performed working directly in the radiofrequency (RF) space. Intuitively, shear-wave displacement is captured by a shift in the radiofrequency signal. By tracking this shift over time, shear-wave displacement can be estimated and then displayed to the user. In this mode, shear modulus and viscosity can be estimated by minimizing the differences between the measured RF shift and a computed RF shift obtained as the difference in the amplitude of the simulated shear displacement at a specific location. One advantage of working directly in the RF space is that the cost function is not affected by any post-processing done on the RF signal when estimating shear-wave displacement. Another advantage of working directly in the RF space is that the measured shear-wave displacement can be automatically smoothed through the fitted model after estimation of the shear-modulus and viscosity (i.e., once the simulated shear-wave propagation converges to the measured shear-wave propagation).

At step 306, it is determined if the simulated shear-wave propagation has converged to the observed shear-wave propagation. For example, a difference value between the simulated and observed shear-wave propagation, as calculated by the cost function, can be compared to a predetermined threshold value. It is determined that the simulated shear-wave propagation has converged to the observed shear-wave propagation when the difference value is less than the threshold value. Otherwise, it is determined that the simulated shear-wave propagation has not converged to the observed shear-wave propagation. In addition, in a possible implementation, the simulated shear-wave propagation can be considered to have converged to the observed shear-wave propagation is a predetermined maximum number of iterations is reached. If it is determined that the simulated shear-wave propagation has not converged to the observed shear-wave propagation, the method proceeds to step 308. If it is determined that the simulated shear-wave propagation has converged to the observed shear-wave propagation, the method proceeds to step 310.

At step 308, the shear modulus and viscosity parameters of the tissue in the target region are estimated by minimizing the cost function. A gradient-free optimizer may be used to calculate new values for the shear modulus and viscosity that minimize the cost function. In an advantageous embodiment, the shear modulus and viscosity values of the tissue is the target region can be calculated using a hierarchical, coarse-to-fine approach to estimate spatial varying parameters for the shear modulus and viscosity. In such a hierarchical approach, in a first step, it is assumed that the tissue in the target region is homogenous and a single value is calculated for each of the shear modulus the viscosity for the entire target region. Then, the spatial domain of the target region is divided in sub-regions based on the spatial distribution of simulation error (e.g., sum of squares distance or NCC error measurement between the computed and measured shear-wave propagation at each point in the spatial domain), shear modulus and viscosity values are estimated separately for each of the sub-regions. In particular, after the initial estimation of shear modulus and viscosity under the assumption of homogenous tissue, another simulation of shear-wave propagation is performed by the computational model using the updated shear modulus and viscosity values and the error (e.g., sum of square difference or NCC) between the computed and observed sheer wave model is calculated at each point in the spatial domain. In an advantageous implementation, the same metric as used to calculated the cost function (e.g., NCC, sum of squared difference, etc.) can be used to calculate the error, but the present invention is not limited thereto, and it is also possible that difference metrics can be used for the cost function evaluation and the error calculation in this step. An error map can be generated by mapping the calculated error value at each point in the spatial domain to an image of the spatial domain. For example, the error map can be an image in which the intensity or color at each pixel depends of the error calculated at that pixel. The error map is segmented to identify regions of the error map having similar error values. The error map can be segmented using any automated or semi-automate image segmentation technique, such as intensity thresholding, region-growing, graph cuts, random walker segmentation, etc. Once the different regions are identified in the error map, a multivariate optimization can be used to estimate different shear modulus and viscosity parameters of each of the identified spatial regions to best minimize the cost function that compares the computed shear-wave propagation to the observed shear-wave propagation. In a possible implementation, this optimization may only be performed for regions having high error values (e.g., higher than a threshold). The steps of generating an error map, segmenting the error map to identify regions having different error values, and calculating the shear modulus and viscosity parameters for the identified regions can be repeated, and at each iteration regions identified in the previous iteration may be divided into smaller regions. These steps can be iterated until the number different regions identified in the spatial domain converges, i.e. the average, or maximum global error is lower than a certain threshold.

Once the spatial-varying shear modulus and viscosity parameters for the tissue in the target region are estimated, the method returns to step 302, and 302, 304, and 306 are repeated with the updated shear modulus and viscosity parameters. In particular, the computational model is used to simulate the shear-wave propagation with the updated shear modulus and viscosity values (step 302), the simulated shear-wave propagation is compared to the observed shear-wave propagation in the shear-wave images using the cost function (step 304), and it is determined whether the simulated shear-wave propagation has converged to the observed shear-wave propagation (step 306).

At step 310, once it is determined that the simulated shear-wave propagation has converged to the observed shear-wave propagation in the shear images, the method of FIG. 3 ends and the final estimated values of the shear modulus and viscosity parameters are returned.

Returning to FIG. 1, at step 106, the estimated shear modulus and viscosity values for the target region are output. The estimated shear modulus and viscosity values can be output by visualizing the shear modulus and viscosity values on 1D, 2D, or 3D maps, which can be displayed on a display device of a computer system. For example, the identified shear modulus values for each location in the spatial domain of the target region of tissue can be mapped to an image of the target region, which is displayed on the display device. The shear modulus values and viscosity values can be visualized using respective color maps, in which the color (or intensity) at each pixel or voxel in the spatial domain depends on the shear modulus value or viscosity value calculated at that location. In a possible implementation, the error maps generated in step 308 of FIG. 3 can be used to generate these color maps, as they are already divided into regions for which common values of shear modulus and viscosity have been calculated.

The spatial maps of shear modulus and viscosity can be displayed to a user (e.g., doctor, technician, etc.) for diagnostic purposes. For example, in oncology applications, the target region in the shear-wave images may include a lesion or tumor, and the estimated patient-specific shear modulus and viscosity values for lesion or tumor can enable the user to diagnose the lesion or tumor as malignant or benign. In a possible application, the values of the shear modulus and viscosity for a lesion or tumor and/or the surrounding region can be used as features and fed into a trained machine learning based classifier, such as a support vector machine (SVM), which can then automatically classify the lesion or tumor. For example, based on the estimated shear modulus and viscosity values, the trained machine learning based classifier could classify the lesion or tumor as malignant or benign, could classify the lesion/tumor as a particular type of lesion/tumor, or could classify the lesion/tumor to assign a particular grade to the lesion/tumor. It is to be understood that the oncology applications described herein are not intended to limit the present invention, and the method of FIG. 1 can also be applied to other applications as well.

Figure 4:
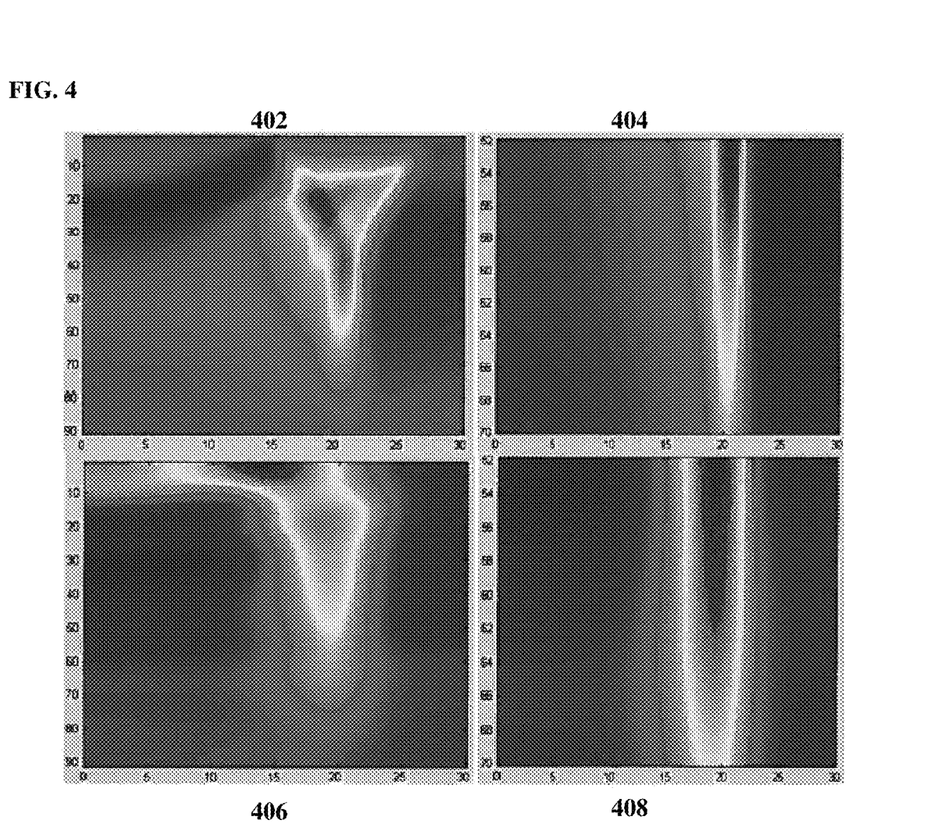
FIG. 4 illustrates exemplary observed and simulated shear-wave propagations after shear modulus and velocity parameter estimation.

In addition to the spatial maps of shear modulus and viscosity, the simulated shear-wave propagation and the shear-wave images showing the observed shear-wave propagation can also be displayed, for example on a display device of a computer system, as well as the error maps generated in step 308 of FIG. 3. FIG. 4 illustrates exemplary observed and simulated shear-wave propagations. As shown in FIG. 4, image 402 shows measured (observed) shear-wave propagation in shear-wave images for the entire spatial domain of the shear-wave images, and image 404 shows the measured (observed) shear-wave propagation for a region of interest used for cost function evaluation. Image 406 shows the simulated shear-wave propagation in the entire spatial domain and image 408 shows the simulated shear-wave propagation in the region of interest used for cost function evaluation. In the example of FIG. 4, the first two frames of the shear-wave images are used as initial conditions for the simulation of shear-wave propagation, and only a portion of the space (region of interest) is used to evaluate the cost function to minimize the effects of the boundary conditions. The ground truth for the properties of the tissue in the region of interest is a shear modulus of 4 kPa and a viscosity of 0 Pa·s. The results of the estimation using the methods of FIGS. 1 and 3 for this example are a shear modulus 4.01 kPa and a viscosity of 4.4 $e^{-10}$ Pa·s. The full space (images 402 and 406 of FIG. 4) shows a difference for the propagation of the waves, but the method still managed to estimate values close to the ground truth values since the evaluation was performed in a region of interest (images 404 and 408 of FIG. 4) far from the boundary conditions.

Figure 5:
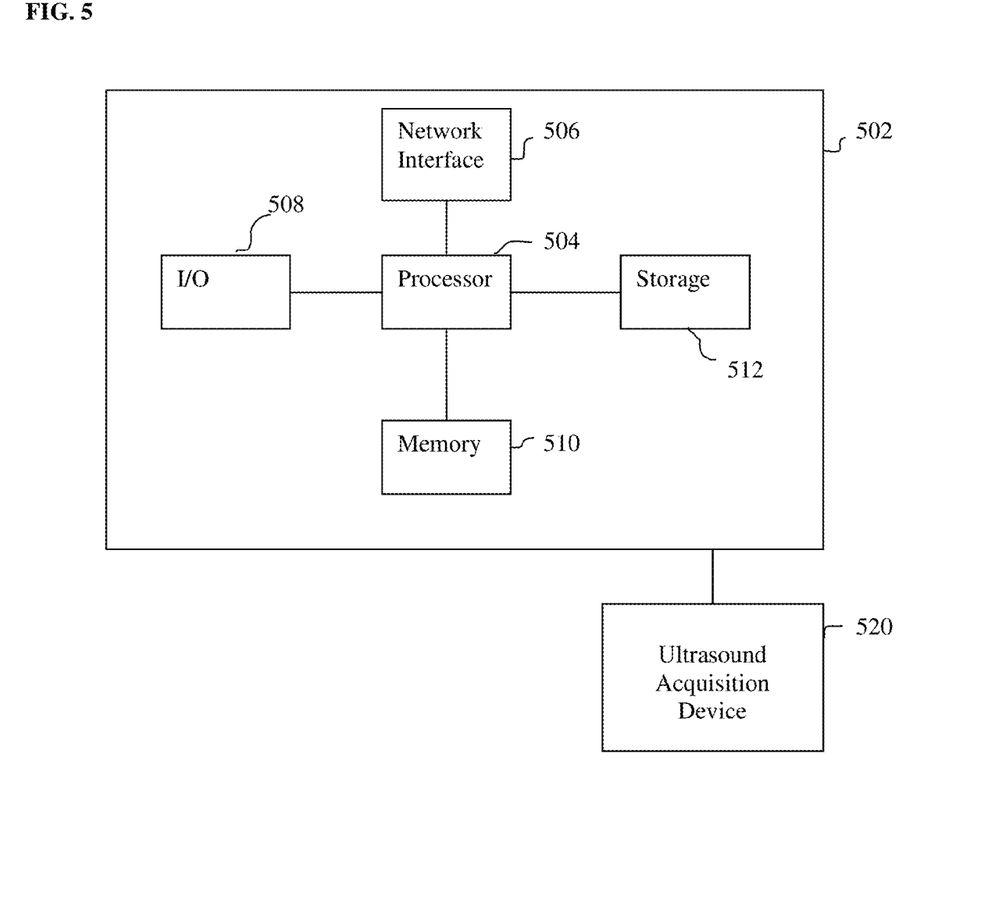
FIG. 5 is a high-level block diagram of a computer capable of implementing the present invention.

The above-described methods for non-invasive estimation of patient-specific shear-modulus and viscosity values for biological tissue based on shear-wave imaging (SWI) can be performed on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the methods of FIGS. 1, 2, and 3 may be defined by the computer program instructions stored in the memory 510 and/or storage 512 and controlled by the processor 504 executing the computer program instructions. An ultrasound acquisition device 520, such as an ultrasound probe, can be connected to the computer 502 to acquire shear wave images and input the shear wave images to the computer 502. It is possible that the ultrasound acquisition device 520 and the computer 502 communicate wirelessly through a network. In a possible embodiment, the computer 502 can be located remotely with respect to the ultrasound acquisition device 520, and the method steps can be performed by the computer 502 as part of a server or cloud based service. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). Such input/output devices 508 may be used in conjunction with a set of computer programs as an annotation tool to annotate volumes received from the image acquisition device 520. One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for estimating shear modulus and viscosity of tissue of a patient based on shear-wave images of the tissue, comprising:
    simulating shear-wave propagation in the tissue based on shear modulus and viscosity values for the tissue using a computational model of shear-wave propagation;
    comparing the simulated shear-wave propagation to observed shear-wave propagation in the shear-wave images of the tissue using a cost function; and
    estimating patient-specific shear modulus and viscosity values for the tissue to optimize the cost function comparing the simulated shear-wave propagation to the observed shear-wave propagation.

2. The method of claim 1, further comprising:
    visualizing the estimated patient-specific shear modulus and viscosity values by generating spatial maps of shear modulus and viscosity.

3. The method of claim 1, wherein simulating shear-wave propagation in the tissue based on shear modulus and viscosity values for the tissue using a computational model of shear-wave propagation comprises:
    computing shear displacement of the tissue in spatial domain corresponding to at least a region of the shear-wave images at each of a plurality of time steps based on the shear modulus and viscosity values for the tissue.

4. The method of claim 3, wherein computing shear displacement of the tissue in spatial domain corresponding to at least a region of the shear-wave images at each of a plurality of time steps based on the shear modulus and viscosity values for the tissue comprises:
    calculating the shear displacement of the tissue in the spatial domain by solving $\rho \partial_t^2 u = \mu \nabla^2 u + \eta \partial_t \nabla^2 u$ at each time step, where $\mu$ is the shear modulus, $\eta$ is the viscosity, $\rho$ is a density of the tissue, and u is shear displacement of the tissue.

5. The method of claim 1, wherein simulating shear-wave propagation in the tissue based on shear modulus and viscosity values for the tissue using a computational model of shear-wave propagation comprises:
    simulating the shear-wave propagation in the tissue using the computational model of shear-wave propagation with predetermined initialized shear modulus and viscosity values for the tissue.

6. The method of claim 1, wherein simulating shear-wave propagation in the tissue based on shear modulus and viscosity values for the tissue using a computational model of shear-wave propagation comprises:
    calculating an initial shear modulus value for the tissue based on a measured shear-wave velocity in the shear-wave images under an assumption that the tissue is non-viscous; and
    simulating the shear-wave propagation in the tissue using the computational model of shear-wave propagation with the calculated initial shear modulus value and a predetermined initial viscosity value.

7. The method of claim 1, wherein simulating shear-wave propagation in the tissue based on shear modulus and viscosity values for the tissue using a computational model of shear-wave propagation comprises:
    determining initial boundary conditions for shear displacement in the tissue based on a number of first frames of the shear wave images; and
    simulating the shear-wave propagation in the tissue starting from the initial boundary conditions for the shear displacement in the tissue based on the shear modulus and viscosity values for the tissue using the computational model of shear-wave propagation.

8. The method of claim 1, wherein simulating shear-wave propagation in the tissue based on shear modulus and viscosity values for the tissue using a computational model of shear-wave propagation comprises:
    determining initial boundary conditions for the shear-wave propagation using a direct model of an acoustic radiation force impulse (ARFI) used to generate the shear-waves in the shear-wave images, wherein the direct model of ARFI is adapted to current probe parameters of an ultrasound probe used to acquire the shear-wave images; and
    simulating the shear-wave propagation in the tissue starting from the initial boundary conditions based on the shear modulus and viscosity values for the tissue using the computational model of shear-wave propagation.

9. The method of claim 1, wherein comparing the simulated shear-wave propagation to observed shear-wave propagation in the shear-wave images of the tissue using a cost function comprises:
    directly comparing a simulated shear-wave displacement to an observed shear-wave displacement at a particular time frame for a plurality of locations in a spatial domain of the shear-wave images using the cost function.

10. The method of claim 9, wherein directly comparing a simulated shear-wave displacement to an observed shear-wave displacement at a particular time frame for a plurality of locations in a spatial domain of the shear-wave images using the cost function comprises:
    calculating a normalized cross-correlation cost function that directly compares the simulated shear-wave displacement to the observed shear-wave displacement at the particular time frame for the plurality of locations in a spatial domain of the shear-wave images.

11. The method of claim 9, wherein directly comparing a simulated shear-wave displacement to an observed shear-wave displacement at a particular time frame for a plurality of locations in a spatial domain of the shear-wave images using the cost function comprises:
    calculating a sum of squared distance cost function that directly compares the simulated shear-wave displacement to the observed shear-wave displacement at the particular time frame for the plurality of locations in the spatial domain of the shear-wave images.

12. The method of claim 1, wherein comparing the simulated shear-wave propagation to observed shear-wave propagation in the shear-wave images of the tissue using a cost function comprises:
  directly comparing a simulated shear-wave displacement to an observed shear-wave displacement for a particular location in a spatial domain of the shear-wave images frame at each of a plurality of time steps using the cost function.

13. The method of claim 1, wherein comparing the simulated shear-wave propagation to observed shear-wave propagation in the shear-wave images of the tissue using a cost function comprises:
  directly comparing a simulated shear-wave displacement to an observed shear-wave displacement for each of a plurality of locations in a spatial domain of the shear-wave images frame at each of a plurality of time steps using the cost function.

14. The method of claim 1, wherein comparing the simulated shear-wave propagation to observed shear-wave propagation in the shear-wave images of the tissue using a cost function comprises:
  calculating a cost function in a radiofrequency space that compares a measured radiofrequency shift of the observed shear-wave propagation with a computed radiofrequency shift of the simulated shear-wave propagation.

15. The method of claim 1, wherein estimating patient-specific shear modulus and viscosity values for the tissue to optimize the cost function comparing the simulated shear-wave propagation to the observed shear-wave propagation comprises:
  estimating an initial shear modulus value and an initial viscosity value for the tissue a target region of the shear-wave images;
  simulating the shear-wave propagation using the computational model of shear-wave propagation with the current values for the shear modulus and viscosity of the tissue in the target region;
  generating an error map showing a spatial distribution of error values between the simulated shear-wave propagation using the current values for the shear modulus and viscosity and the observed spatial propagation;
  segmenting the error map to identify sub-regions of tissue within the target region based on the error values between the simulated shear-wave propagation using the current values for the shear modulus and viscosity and the observed spatial propagation; and
  estimating spatially-varying shear modulus and viscosity values for the tissue in the target region by calculating separate values for the shear modulus and viscosity for each of the identified sub-regions of tissue to optimize the cost function using a multivariate optimization.

16. The method of claim 15, wherein estimating patient-specific shear modulus and viscosity values for the tissue to optimize the cost function comparing the simulated shear-wave propagation to the observed shear-wave propagation further comprises:
  repeating the steps of simulating the shear-wave propagation using the computational model of shear-wave propagation with the current values for the shear modulus and viscosity of the tissue in the target region, generating an error map, segmenting the error map, and estimating spatially-varying shear modulus and viscosity values for the tissue in the target region until a number of the sub-regions in the target region converges.

17. The method of claim 1, further comprising:
  repeating the steps of simulating shear-wave propagation in the tissue based on shear modulus and viscosity values for the tissue using a computational model of shear-wave propagation, comparing the simulated shear-wave propagation to observed shear-wave propagation in the shear-wave images of the tissue using a cost function, and estimating patient-specific shear modulus and viscosity values for the tissue to optimize the cost function comparing the simulated shear-wave propagation to the observed shear-wave propagation, until the simulated shear-wave propagation converges to the observed shear-wave propagation in the shear wave images.

18. The method of claim 2, wherein the estimated patient-specific shear modulus values and viscosity values for the tissue are spatially varying shear modulus values and viscosity values, and visualizing the estimated patient-specific shear modulus and viscosity values by generating spatial maps of shear modulus and viscosity comprises:
  generating a shear modulus color map by mapping the estimated spatially varying patient-specific shear modulus values to a spatial domain of the shear-wave images and assigning a color to each pixel in the shear modulus color map based on the estimated patient-specific shear modulus value for that pixel; and
  generating a viscosity color map by mapping the estimated spatially varying patient-specific viscosity values to the spatial domain of the shear-wave images and assigning a color to each pixel in the viscosity color map based on the estimated patient-specific viscosity value for that pixel.

19. A non-transitory computer readable medium storing computer program instructions for estimating shear modulus and viscosity of tissue of a patient based on shear-wave images of the tissue, the computer program instructions when executed by a processor cause the processor to perform operations comprising:
  simulating shear-wave propagation in the tissue based on shear modulus and viscosity values for the tissue using a computational model of shear-wave propagation;
  comparing the simulated shear-wave propagation to observed shear-wave propagation in the shear-wave images of the tissue using a cost function; and
  estimating patient-specific shear modulus and viscosity values for the tissue to optimize the cost function comparing the simulated shear-wave propagation to the observed shear-wave propagation.

20. The non-transitory computer readable medium of claim 19, wherein the operations further comprise:
  visualizing the estimated patient-specific shear modulus and viscosity values by generating spatial maps of shear modulus and viscosity.

21. The non-transitory computer readable medium of claim 19, wherein simulating shear-wave propagation in the tissue based on shear modulus and viscosity values for the tissue using a computational model of shear-wave propagation comprises:
  computing shear displacement of the tissue in spatial domain corresponding to at least a region of the shear-wave images at each of a plurality of time steps based on the shear modulus and viscosity values for the tissue.

22. The non-transitory computer readable medium of claim 21, wherein computing shear displacement of the tissue in spatial domain corresponding to at least a region of the shear-wave images at each of a plurality of time steps based on the shear modulus and viscosity values for the tissue comprises:

calculating the shear displacement of the tissue in the spatial domain by solving $\rho \partial_t^2 u = \mu \nabla^2 u + \eta \partial_t \nabla^2 u$ at each time step, where $\mu$ is the shear modulus, $\eta$ is the viscosity, $\rho$ is a density of the tissue, and u is shear displacement of the tissue.

23. The non-transitory computer readable medium of claim 19, wherein simulating shear-wave propagation in the tissue based on shear modulus and viscosity values for the tissue using a computational model of shear-wave propagation comprises:

simulating the shear-wave propagation in the tissue using the computational model of shear-wave propagation with predetermined initialized shear modulus and viscosity values for the tissue.

24. The non-transitory computer readable medium of claim 19, wherein simulating shear-wave propagation in the tissue based on shear modulus and viscosity values for the tissue using a computational model of shear-wave propagation comprises:

calculating an initial shear modulus value for the tissue based on a measured shear-wave velocity in the shear-wave images under an assumption that the tissue is non-viscous; and simulating the shear-wave propagation in the tissue using the computational model of shear-wave propagation with the calculated initial shear modulus value and a predetermined initial viscosity value.

25. The non-transitory computer readable medium of claim 19, wherein simulating shear-wave propagation in the tissue based on shear modulus and viscosity values for the tissue using a computational model of shear-wave propagation comprises:

determining initial boundary conditions for shear displacement in the tissue based on a number of first frames of the shear wave images; and simulating the shear-wave propagation in the tissue starting from the initial boundary conditions for the shear displacement in the tissue based on the shear modulus and viscosity values for the tissue using the computational model of shear-wave propagation.

26. The non-transitory computer readable medium of claim 19, wherein simulating shear-wave propagation in the tissue based on shear modulus and viscosity values for the tissue using a computational model of shear-wave propagation comprises:

determining initial boundary conditions for the shear-wave propagation using a direct model of an acoustic radiation force impulse (ARFI) used to generate the shear-waves in the shear-wave images, wherein the direct model of ARFI is adapted to current probe parameters of an ultrasound probe used to acquire the shear-wave images; and simulating the shear-wave propagation in the tissue starting from the initial boundary conditions based on the shear modulus and viscosity values for the tissue using the computational model of shear-wave propagation.

27. The non-transitory computer readable medium of claim 19, wherein comparing the simulated shear-wave propagation to observed shear-wave propagation in the shear-wave images of the tissue using a cost function comprises:

directly comparing a simulated shear-wave displacement to an observed shear-wave displacement at a particular time frame for a plurality of locations in a spatial domain of the shear-wave images using the cost function.

28. The non-transitory computer readable medium of claim 27, wherein directly comparing a simulated shear-wave displacement to an observed shear-wave displacement at a particular time frame for a plurality of locations in a spatial domain of the shear-wave images using the cost function comprises:

calculating one of a normalized cross-correlation cost function or a sum of squared distance cost function that directly compares the simulated shear-wave displacement to the observed shear-wave displacement at the particular time frame for the plurality of locations in a spatial domain of the shear-wave images.

29. The non-transitory computer readable medium of claim 19, wherein comparing the simulated shear-wave propagation to observed shear-wave propagation in the shear-wave images of the tissue using a cost function comprises:

directly comparing a simulated shear-wave displacement to an observed shear-wave displacement for a particular location in a spatial domain of the shear-wave images frame at each of a plurality of time steps using the cost function.

30. The non-transitory computer readable medium of claim 19, wherein comparing the simulated shear-wave propagation to observed shear-wave propagation in the shear-wave images of the tissue using a cost function comprises:

directly comparing a simulated shear-wave displacement to an observed shear-wave displacement for each of a plurality of locations in a spatial domain of the shear-wave images frame at each of a plurality of time steps using the cost function.

31. The non-transitory computer readable medium of claim 19, wherein comparing the simulated shear-wave propagation to observed shear-wave propagation in the shear-wave images of the tissue using a cost function comprises:

calculating a cost function in a radiofrequency space that compares a measured radiofrequency shift of the observed shear-wave propagation with a computed radiofrequency shift of the simulated shear-wave propagation.

32. The non-transitory computer readable medium of claim 19, wherein estimating patient-specific shear modulus and viscosity values for the tissue to optimize the cost function comparing the simulated shear-wave propagation to the observed shear-wave propagation comprises:

estimating an initial shear modulus value and an initial viscosity value for the tissue a target region of the shear-wave images;

simulating the shear-wave propagation using the computational model of shear-wave propagation with the current values for the shear modulus and viscosity of the tissue in the target region;

generating an error map showing a spatial distribution of error values between the simulated shear-wave propagation using the current values for the shear modulus and viscosity and the observed spatial propagation;

segmenting the error map to identify sub-regions of tissue within the target region based on the error values between the simulated shear-wave propagation using the current values for the shear modulus and viscosity and the observed spatial propagation; and estimating spatially-varying shear modulus and viscosity values for the tissue in the target region by calculating separate values for the shear modulus and viscosity for each of the identified sub-regions of tissue to optimize the cost function using a multivariate optimization.

33. The non-transitory computer readable medium of claim 32, wherein estimating patient-specific shear modulus and viscosity values for the tissue to optimize the cost function comparing the simulated shear-wave propagation to the observed shear-wave propagation further comprises:
repeating the operations of simulating the shear-wave propagation using the computational model of shear-wave propagation with the current values for the shear modulus and viscosity of the tissue in the target region, generating an error map, segmenting the error map, and estimating spatially-varying shear modulus and viscosity values for the tissue in the target region until a number of the sub-regions in the target region converges.

34. The non-transitory computer readable medium of claim 19, where the operations further comprise:
repeating the operations of simulating shear-wave propagation in the tissue based on shear modulus and viscosity values for the tissue using a computational model of shear-wave propagation, comparing the simulated shear-wave propagation to observed shear-wave propagation in the shear-wave images of the tissue using a cost function, and estimating patient-specific shear modulus and viscosity values for the tissue to optimize the cost function comparing the simulated shear-wave propagation to the observed shear-wave propagation, until the simulated shear-wave propagation converges to the observed shear-wave propagation in the shear wave images.

35. The non-transitory computer readable medium of claim 20, wherein the estimated patient-specific shear modulus values and viscosity values for the tissue are spatially varying shear modulus values and viscosity values, and visualizing the estimated patient-specific shear modulus and viscosity values by generating spatial maps of shear modulus and viscosity comprises:
generating a shear modulus color map by mapping the estimated spatially varying patient-specific shear modulus values to a spatial domain of the shear-wave images and assigning a color to each pixel in the shear modulus color map based on the estimated patient-specific shear modulus value for that pixel; and
generating a viscosity color map by mapping the estimated spatially varying patient-specific viscosity values to the spatial domain of the shear-wave images and assigning a color to each pixel in the viscosity color map based on the estimated patient-specific viscosity value for that pixel.

* * * * *